(12) United States Patent
Eger et al.

(10) Patent No.: US 10,406,307 B2
(45) Date of Patent: Sep. 10, 2019

(54) METHOD AND DEVICE FOR GENERATING A CONTROL SIGNAL FOR A VENTILATOR

(71) Applicant: Drägerwerk AG & Co. KGaA, Lübeck (DE)

(72) Inventors: Marcus Eger, Lübeck (DE); Lorenz Kahl, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 669 days.

(21) Appl. No.: 14/916,435

(22) PCT Filed: Sep. 5, 2014

(86) PCT No.: PCT/EP2014/002409
§ 371 (c)(1),
(2) Date: Mar. 3, 2016

(87) PCT Pub. No.: WO2015/032504
PCT Pub. Date: Mar. 12, 2015

(65) Prior Publication Data
US 2016/0199606 A1 Jul. 14, 2016

(30) Foreign Application Priority Data
Sep. 6, 2013 (EP) ..................... 13183413

(51) Int. Cl.
*A61M 16/00* (2006.01)
*A61B 5/0488* (2006.01)
(Continued)

(52) U.S. Cl.
CPC ....... *A61M 16/0069* (2014.02); *A61B 5/0488* (2013.01); *A61B 5/08* (2013.01);
(Continued)

(58) Field of Classification Search
CPC .............. A61M 16/00; A61M 16/0069; A61M 16/026; A61B 5/08; A61B 5/04; A61B 5/0488; A61B 5/6823
See application file for complete search history.

(56) References Cited

U.S. PATENT DOCUMENTS

| 4,915,103 | A | 4/1990 | Visveshwara et al. |
| 9,238,114 | B2 | 1/2016 | Eger et al. |

(Continued)

FOREIGN PATENT DOCUMENTS

| DE | 699 21 782 T2 | 10/2005 |
| DE | 10 2007 062214 B3 | 8/2009 |

(Continued)

*Primary Examiner* — Jan Christopher L Merene
*Assistant Examiner* — Cana A Gallegos
(74) *Attorney, Agent, or Firm* — McGlew and Tuttle, P.C.

(57) ABSTRACT

A ventilator control signaling method includes recording an electromyogram signal of values following one another in time and transforming the electromyogram signal into an evaluation signal by applying an evaluation function. An evaluation signal value is assigned to a signal value of the electromyogram signal in the transformation. The evaluation function is determined by a main parameter set that defines which signal value of the evaluation signal is assigned to a particular signal value of the electromyogram signal when the evaluation function is applied in the transformation. A signal value height of the evaluation signal indicates whether the electromyogram signal corresponds to a first state or a second state. A control signal is generated from signal values and is set to switch a ventilator to an inhalation or an exhalation operating mode depending on the state of the evaluation signal. A ventilator is configured to perform the method.

13 Claims, 4 Drawing Sheets

(51) Int. Cl.
*A61B 5/08* (2006.01)
*A61B 5/00* (2006.01)
(52) U.S. Cl.
CPC ......... *A61M 16/026* (2017.08); *A61B 5/6823* (2013.01); *A61M 2230/60* (2013.01)

(56) References Cited

U.S. PATENT DOCUMENTS

| | | |
|---|---|---|
| 2005/0081855 A1 | 4/2005 | Berthon-Jones |
| 2009/0159082 A1 | 6/2009 | Eger |
| 2012/0152249 A1* | 6/2012 | Eger ................ A61M 16/00 128/204.23 |
| 2014/0142395 A1* | 5/2014 | Sattler ................ A61B 5/7203 600/300 |

FOREIGN PATENT DOCUMENTS

| | | |
|---|---|---|
| DE | 10 2010 055 243 A1 | 6/2012 |
| DE | 10 2010 055242 A1 | 6/2012 |
| EP | 1 056 499 B1 | 11/2004 |
| EP | 2465562 A1 | 6/2012 |
| WO | 99/43374 A1 | 9/1999 |
| WO | 01/19440 A1 | 3/2001 |
| WO | 02/094358 A1 | 11/2002 |

\* cited by examiner

METHOD AND DEVICE FOR GENERATING A CONTROL SIGNAL FOR A VENTILATOR

CROSS REFERENCE TO RELATED APPLICATIONS

This application is a United States National Phase Application of International Application PCT/EP2014/002409 filed Sep. 5, 2014 and claims the benefit of priority under 35 U.S.C. § 119 of European Patent Application 13 183 413.7 filed Sep. 6, 2013, the entire contents of which are incorporated herein by reference.

FIELD OF THE INVENTION

The present invention pertains to a method as well as to a device for generating a control signal for a ventilator (also known as a respirator).

BACKGROUND OF THE INVENTION

A ventilator, by means of which a patient is mechanically ventilated, can be actuated with such a method, and a control signal, which switches the ventilator between a phase of inhalation, during which breathing air is fed to the patient, and a phase of exhalation, during which the patient exhales, is generated from the measured signal, which is obtained at the patient. When the patient is making efforts, albeit insufficiently, on his own to inhale and when he fails to exhale are determined from the measured signal.

It is already known in this connection from the state of the art that flow sensors can be used, which detect the volume flow in a tube section between the ventilator and the patient, and the ventilator will then be switched into the phase of inhalation or the phase of exhalation depending on the direction and the value of this volume flow.

Such a procedure is, however, disadvantageous, because it is necessary for a switch-over that the patient must have made a comparatively great effort to bring about a measurable change in the volume flow, and this effort will then cause the ventilator to be switched over. Another drawback is that the switch-over takes place only when the patient has already made efforts and was not supporting the breathing at an earlier point time already.

It is desirable against the background to use another physiological signal, which is markedly more sensitive to the start of the breathing efforts than a volume flow signal, instead of the volume flow signal for controlling the ventilator.

It is already known in this connection from the state of the art, for example, EP 1 056 499 B1 or U.S. Pat. No. 4,915,103, that the electromyogram signal can be used, but the problem arises here that the signal detected with electrodes on the body surface or, as is disclosed in EP 1 056 499 B1, with an electrode in the trachea, has a considerable interference component. In addition, the potentials, which are detected in the process and with which muscles that are relevant for breathing are stimulated, are very low. Especially compared to the cardiac signals (EKG signals), these signals are lower by several orders of magnitude, so that the cardiac signals represent major artifacts.

Great efforts are therefore needed to detect in the electromyogram signal the transition between a phase, during which no efforts are being made by the patient and which reflects the phase of exhalation and a phase of inhalation, during which the muscles relevant for breathing are stimulated. However, the electromyogram signal, which is sensitive to a change in the stimulation potentials for the muscles relevant for breathing, offers the great advantage that the start of the breathing efforts can be detected with this signal very well.

However, the state of the art fails to offer any reliable methods with which a distinction can be made between the phase of inhalation and the phase of exhalation in an electromyogram signal recorded in the area of the muscles relevant for breathing and on the basis of which a ventilator can be actuated.

SUMMARY OF THE INVENTION

Therefore, based on the state of the art, an object of the present invention is to provide a method and a device for generating a control signal for a ventilator on the basis of an electromyogram signal, which reliably determines the transition between the phase of inhalation and the phase of exhalation.

This object is accomplished by a method comprising the following steps:

Detection of an electromyogram signal, which comprises signal values following one another in time, Transformation of the electromyogram signal into an evaluation signal by applying an evaluation function to the electromyogram signal, wherein a signal value of the evaluation signal is assigned to a signal value of the electromyogram signal during the transformation, wherein the evaluation function is determined by a main parameter set, so that the main parameter set determines which signal value of the evaluation signal is assigned to which signal value of the electromyogram signal during the transformation when applying the evaluation function, and wherein the height of the signal value of the evaluation signal indicates whether the electromyogram signal corresponds to a first state or to a second state, and Generation of a control signal from signal values following one another in time, which is adapted to switch a ventilator into an inhalation operating mode if the evaluation signal corresponds to the first state and into an exhalation operating mode if the evaluation signal corresponds to the second state.

Analogously, the device according to the present invention has, in addition to a signal input for detecting the electromyogram signal, the corresponding means for carrying out the aforementioned method steps.

A signal value of an evaluation signal is determined in the method according to the present invention and with the device according to the present invention by using an evaluation function, which is determined, in turn, by a main parameter set, for each signal value of the electromyogram signal, so that the signal value of the evaluation signal is unambiguously defined via the main parameter set. The signal value of the evaluation signal is an indicator indicating whether the signal value in question is to be assigned to the phase of inhalation or to the phase of exhalation.

The evaluation function may be especially a function of the ratio of the probabilities $P_I(x)$, $P_E(x)$ that the signal value x in question belongs to the phase of inhalation and to the phase of exhalation, and it is especially preferred if the logarithm of the quotient $\log(P_I(x)/P_E(x))$ of these probabilities is used. The values for $P_I(x)$ and $P_E(x)$ or the quotient of the logarithm will then form at least partly the main parameter set, and the evaluation function assigns in this case the signal value x to the corresponding value for the logarithm from the quotient of the probabilities $P_I(x)$; $P_E(x)$.

If the probability $P_I(x)$ for the phase of inhalation is greater than that for the phase of exhalation, $P_E(x)$, the quotient is greater than 1, so that the logarithm is greater than 0. Conversely, the evaluation function is lower than 0 if the probability $P_E(x)$ that the value x belongs to the phase of exhalation is greater than the probability $P_I(x)$ that it is detected in the phase of inhalation, because the quotient $(P_I(x)/P_E(x))$ is now lower than 1. It can therefore be determined in a simple manner by a subsequent threshold value comparison with the threshold value zero whether the phase of inhalation or the phase of exhalation is present.

The transformation with the use of an evaluation function creates, on the whole, the possibility that the detected signal values are evaluated according to which of the two phases they belong to. The parameter set may be adapted to the particular patient and the conditions under which the electromyogram signal is detected. In particular, the possibility of adapting the parameter set to changing conditions even during the ongoing method is created. In any case, it is, however, achieved by the variable parameter set that the method does not generate, for example, a control signal simply on the basis of a comparison with a threshold value predefined as a fixed value, but can operate flexibly.

The present invention may also be applied, in particular, in such a way that a method for ventilating a patient is obtained thereby, in which an electromyogram signal is detected at the patient, and a ventilator connected to the patient is actuated with the control signal thus generated on the basis of this signal in the above-described manner.

Further, it is preferred if either the electromyogram signal or the evaluation signal generated by transformation is smoothed. This can be carried out in such a way that each signal value of the electromyogram signal or of the evaluation signal is treated as a predefined signal value and each predefined signal value of the electromyogram signal or of the evaluation signal is replaced by a mean value from signal values of the respective signal, which signal values may comprise the predefined signal value and comprise a first number of signal values that precede in time the determined signal value.

Peaks in the respective signal are eliminated by such smoothing. It should be noted here that the term "mean value" shall cover not only the arithmetic mean. This term rather also covers the situation in which the mean value can be formed in such a way that the individual signal values from a first number are included in the formation of the mean value with different weightings. Moreover, the term "mean value" shall also cover in the sense of the present invention such values that are obtained by applying nonlinear smoothing methods such as rank filters or median filters.

The procedure followed in this preferred embodiment of the method according to the present invention is that the signal values of the electromyogram signal or of the evaluation signal are processed in such a way that they are treated as predefined signal values in the order in which they were detected or, for the signal values of the evaluation signals, in which the corresponding electromyogram signals were detected. A mean value is then formed for each predefined signal value from a first number of signal values detected before the predefined signal value and the predefined signal value is replaced by this mean value.

This means that the first number of signal values comprises values for which the above-described averaging was already performed. This may be associated with the drawback that if this smoothing method is applied to the evaluation signal, a rise or drop in the smoothed signal will develop there with a delay only. This is due to the fact that the value of a predefined signal value rises after smoothing and the replacement by the mean value only when the values preceding this predefined signal value in time are also already increased in order for this to correspondingly affect the mean value.

To eliminate this problem at least partially, the mean value can be formed in such a way that values located in time close to the predefined signal value are included in the averaging in a weighted form as such from the first number of signal values, which are located farther before the predefined signal value in time.

The main parameter set is preferably in the form of a table, i.e., the device is also designed correspondingly to store the main parameter set as a table, in which the assigned signal value for the evaluation signal is contained for each possible signal value of the electromyogram signal, and wherein the value corresponding to the table is assigned as a signal value of the evaluation signal to a signal value of the electromyogram signal when using the evaluation function.

Such a table makes possible, on the one hand, fast processing of the continuously detected electromyogram signal. On the other hand, the table can easily be overwritten if the conditions have changed during the run of the method during the control of the ventilator, so that the assignment of the signal values to the phase of inhalation and to the phase of exhalation is different.

Further, it is preferred if each signal value of the evaluation signal is compared to a threshold value when the control signal is generated, the control signal assuming a first control value if the signal value of the evaluation signal is above the threshold value, and the control signal assuming a second control value if the signal value of the evaluation signal is below the threshold value.

The control signal can be generated simply and rapidly in this way. The threshold value can now be adapted to the evaluation function. For example, the threshold value equals zero if the logarithm of the quotient of the probabilities $P_I(x)$, $P_E(x)$ that the signal value x of the electromyogram signal belongs to the phase of inhalation or to the phase of exhalation is used as the evaluation function. Nevertheless, the method can be adapted to changed conditions by adapting the main parameter set. However, this possibility does not lead to a slowdown of the generation of the control signal.

As was already explained, it is preferred that if the evaluation function is applied to signal values x from a range around a base value, a signal value of the evaluation signal is assigned, which signal value is a function of the ratio of the probability $P_1(x)$ that the signal value x corresponds to the first state to the probability $P_2(x)$ that the signal value x corresponds to the second state. In another preferred manner, this function may be the logarithm, which will then cause, as was already explained, the value zero to be a suitable threshold value, so that the generation of the control signal can be managed in a simple manner.

Outside the range in question for the signal values of the electromyogram signal around the base value, the evaluation function can be defined such that a constant value or at first linearly increasing values and then a constant value are used here.

Finally, it should also be noted in this connection that it is also possible when carrying out the method according to the present invention that the electromyogram signal is processed prior to the step of transformation in such a way that a constant background is subtracted in order for the signal thus processed to subsequently vary around zero. The base value is equal to zero in this connection in such a case or in the case in which the electromyogram signal varies by itself around zero.

The main parameter set is continuously determined anew in an especially preferred embodiment of the method and in the corresponding device and is thus adapted to the conditions time and time again during the run of the method and during the operation of the device. The following steps are carried out in this embodiment simultaneously with the transformation of the electromyogram signal and the generation of the control signal:

Transformation of an analysis segment of the electromyogram signal into a second evaluation signal by applying the evaluation function to the analysis segment, a signal value of the second evaluation signal being assigned to a signal value of the analysis segment during the transformation, wherein the evaluation function is determined by an analysis parameter set, so that the analysis parameter set determines which signal value of the second evaluation signal is assigned to which signal value of the analysis segment during the transformation when using the evaluation function, and wherein the height of the signal value of the second evaluation signal indicates whether the corresponding signal value of the analysis segment corresponds to a first state or to a second state, Determination of a first frequency distribution for the signal values from the parts of the analysis segment, for which the second evaluation signal indicates that the first state is present, Determination of a second frequency distribution for the signal values from the parts of the analysis segment, for which the second evaluation signal indicates that the second state is present, Determination of a renewed parameter set from the frequency distributions, and Transfer of the renewed parameter set as a main parameter set.

The corresponding means are then provided in the device according to the present invention. Accordingly, the main parameter set underlying the transformation is determined simultaneously with the transformation of the electromyogram signal and to the generation of the control signal in such a way that the electromyogram signal, namely, a segment thereof, namely, the analysis segment, is transformed at first into a second evaluation signal for this as well. Those segments in which the first state, i.e., the phase of inhalation, is present, and those segments in which the second state, i.e., the phase of exhalation, is present, are then determined in the analysis segment. Finally, the segments are analyzed separately.

This is carried out in such a way that the evaluation function already described, which is determined by an analysis parameter set in this case, is applied to the signal values of the analysis segment. A standard parameter set is preferably used here for the evaluation function or the main parameter set that just happens to be current is used as the analysis parameter set. A standard parameter set can be determined here in such a way that the magnitude of the input signal is determined at first over a time period, which is markedly greater than the reciprocal value of the respiration rate. This magnitude is greatly smoothed and subsequently compared to the input signal. The standard parameter set is set now such that signal values with a magnitude below the smoothed magnitude are assigned to the phase of exhalation, whereas signal values with a magnitude above the smoothed magnitude are assigned to the phase of inhalation.

In another preferred manner, those signal values of the analysis segment for which the signal value of the evaluation signal is above a threshold and those for which the signal value is below the threshold are subsequently determined.

The signal values of the analysis segment, at which the corresponding signal value of the evaluation signal exceeds the threshold are marked as belonging to the first state, namely, the phase of inhalation, while those signal values of the analysis segment at which the signal values of the second evaluation signal are below the threshold are marked as belonging to the second state, i.e., the phase of exhalation.

An analysis, during which a first frequency distribution is established for the signal values, is subsequently performed separately for those signal values of the analysis segment that were marked as belonging to the first state and hence to the phase of inhalation. This first frequency distribution is then proportional to the probability $P_I(x)$ that a signal value x belongs to the phase of inhalation. A second frequency distribution, which will then indicate an indicator for the probability $P_E(x)$ that a signal x belongs to the phase of exhalation, is established in the same manner for those signal values that were marked as belonging to the second state, i.e., the phase of exhalation.

A renewed parameter set can then be determined from the first and second frequency distributions, and this is carried out in an especially preferred manner by the renewed parameter set being designed as a table, which assigns a signal value of the second evaluation signal to each possible signal value of the electromyogram signal, and the assigned signal value of the table is a function of the ratio of the value of the first frequency distribution for the signal value x to the value of the second frequency distribution for the signal value x for a signal value y of the electromyogram signal, which signal value is located in a range around a base value. If a constant background is subtracted at first in an electromyogram signal before the further processing, the base value equals zero here as well. The function of the quotient may be the logarithm for the reasons already described.

Finally, the table may contain, in another preferred manner, a constant value as an assigned signal value for signal values x of the analysis segment or of the electromyogram signal from a marginal range, which is located outside the range.

In addition, the parameter set may be replaced or estimated by simplified function curves, i.e., constants, linear functions or other simple functions in ranges located far away from the base value, in which there are only inaccurate estimates of the frequency distributions because of very rare probabilities of occurrence.

When this process is concluded for a predefined analysis segment, the renewed parameter set thus obtained can be used and correspondingly transferred as a main parameter set.

This procedure creates the possibility of continually optimizing the main parameter set, which is used when generating the control signal, or to adapt it to changes in the patient, which may arise, for example, due to the fact that the electromyogram signal changes or is shifted due to a motion of the patient.

It is therefore also preferred, as was already mentioned, that the main parameter set is used at first for the evaluation function and the assignment of the individual parts of the analysis segment to the phase of exhalation and the phase of inhalation when determining the parameter set in an analysis segment of the electromyogram signal. Thus, an iterative procedure is then implemented.

Finally, the assignment of the signal values of the analysis segment to the first state and to the second state may be effected by an analysis signal. The device preferably has corresponding means for generating such an analysis signal. This analysis signal, which contains an analysis signal value for each signal value of the analysis segment, is generated in such a way that an analysis signal value assumes a first value if the signal value of the second evaluation signal that corresponds to the signal value of the analysis segment, for which the analysis signal value is generated, is above a threshold value, and that an analysis signal value assumes a second value if the signal value of the second evaluation signal, which corresponds to the signal value of the analysis segment, for which the analysis signal value is generated, is below a threshold value. The first frequency distribution is determined for the signal values of the analysis segment for which the analysis signal value has the first value, and the second frequency distribution is determined for the signal values of the analysis segment, for which the analysis signal value has the second value.

In another preferred manner, the second evaluation signal is smoothed during the determination of the parameter set, and the averaging is performed here over a greater second number of signal values compared to the smoothing during the determination of the control signal. The procedure followed during the smoothing otherwise corresponds to that already described in connection with the smoothing of the electromyogram signal and of the first evaluation signal during the generation of the control signal.

Nevertheless, the greater second number of signal values, which are taken into account during the smoothing, will then cause the determination of the parameter set to take place comparatively slowly. However, this is not disadvantageous at all, and it should be borne mind that a higher accuracy is also achieved in the determination of the frequency distributions due to the greater smoothing.

Finally, it is preferred, when determining the parameter set, to carry out the classification that determines which parts of the analysis segment belong to the phase of inhalation and which parts belong to the phase of exhalation with an analysis signal, which is binary, similarly to the control signal, and thus characterizes the individual parts.

The present invention will be explained below on the basis of drawings, which show only a preferred exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENTS

An exemplary embodiment of a method according to the present invention is explained in detail on the basis of the drawings. In addition to a schematic flow chart of the entire method according to the preferred exemplary embodiment, FIG. 1 also shows schematically the design of a corresponding device 2 for generating a control signal, which device is equipped with the corresponding means for carrying out the method steps, an exemplary embodiment of such a device 2 also being shown in FIG. 4.

Figure 1:
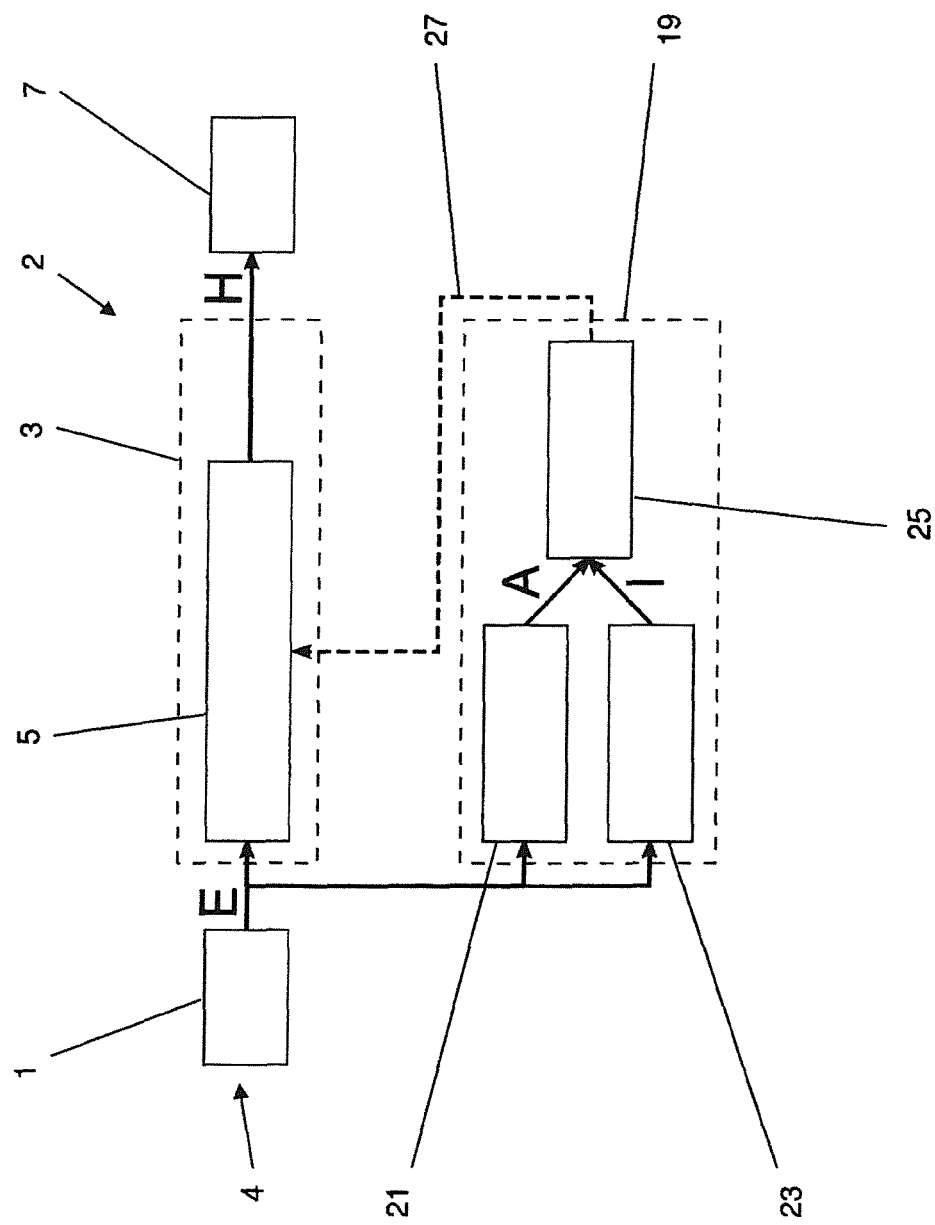
FIG. 1 is a flow chart of the exemplary embodiment of a method according to the present invention, according to which the exemplary embodiment of a device according to the present invention is operated.

As can also be seen in FIG. 1, an electromyogram signal of a patient is recorded in the exemplary embodiment in a first detection step 1. This signal can be detected in a manner known per se by means of electrodes placed on the skin of the patient in the area of the thorax.

Before the signal is processed further, a constant background or a background varying only slowly over time may be subtracted from the electromyogram signal in detection step 1, so that the signal then obtained varies essentially around a signal value of zero. Such an electromyogram signal is designated by "E" in FIG. 2.

The electromyogram signal E, which is thus obtained and is freed from a possible background, is sent to a so-called control signal path 3 or primary segmentation path, and a signal input 4 is provided in the device 2, via which the raw signal is sent to the device 2 before a possible correction of the background.

The control signal path 3 comprises a step 5 for generating a control signal for a ventilator 7, which may be connected to a patient. This step 5 of generating the control signal is shown in detail in FIG. 2, and the control signal H being shown here is suitable for switching the ventilator 7 to and fro between an inhalation operating mode, in which breathing gas is actively fed to the patient, and an exhalation operating mode. It must be determined for this from the electromyogram signal E whether its corresponding signal value x corresponds to a first state of the patient, on the one hand, in which the patient is making breathing efforts and the potentials on the muscles relevant for breathing are therefore increased, i.e., the phase of inhalation is occurring. On the other hand, a second state may also occur in the patient, in which the patient is not making any breathing efforts, i.e., the phase of exhalation is present, which is reflected in reduced potentials on the muscles relevant for breathing.

The control signal obtained in the process is designated by "H": in FIG. 2, and it will be explained below how this control signal H is generated in the method according to the present invention in the control signal or primary segmentation path 3 in step 5.

Figure 2:
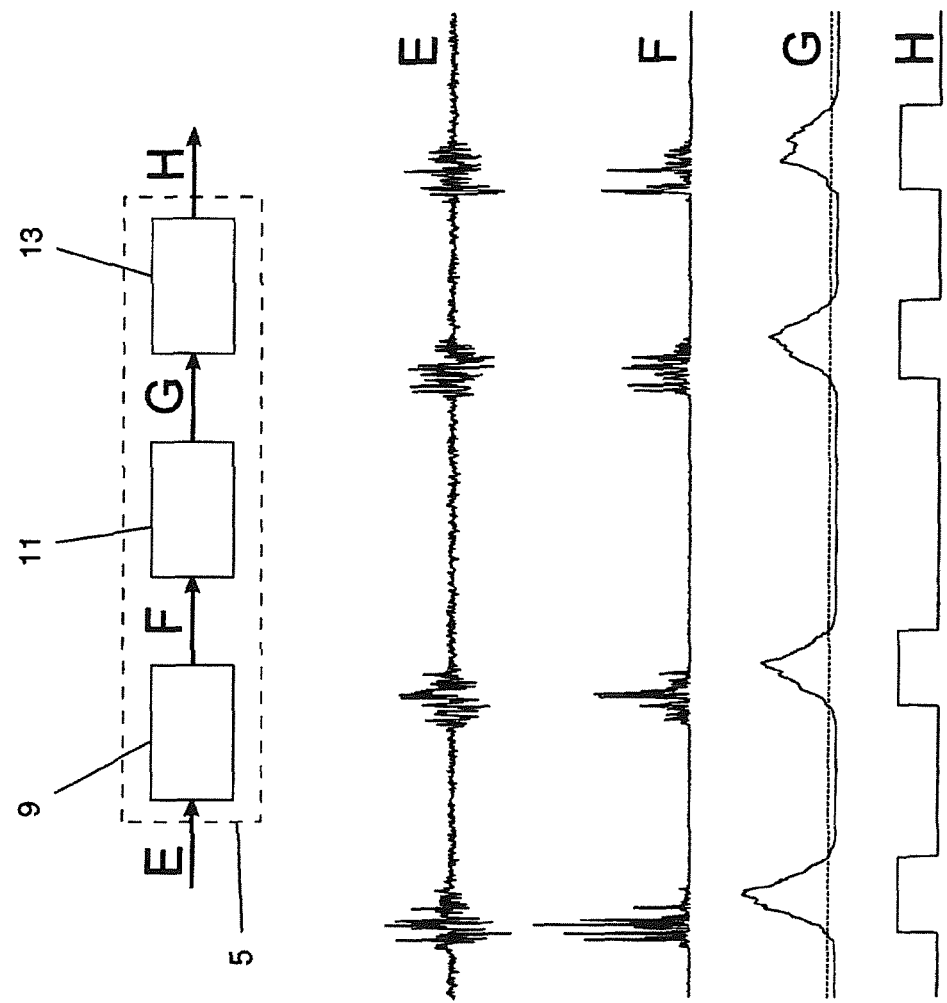
FIG. 2 is a part of the flow chart from FIG. 1 in detail together with the signals generated in the process as a function of time.

As can be seen in FIG. 2, a transformation step 9, in which the electromyogram signal E is transformed into an evaluation signal F by applying an evaluation function to the electromyogram signal E, is carried out at first in step 5. A signal value y of the evaluation signal F is assigned in this transformation step 9 to each signal value x of the electromyogram signal E, the evaluation function being determined by a main parameter set, so that the main parameter set determines which signal value y of the evaluation signal F is assigned to which signal value x of the electromyogram signal E during the transformation when applying the evaluation function.

The main parameter set is present in the preferred exemplary embodiment being described here as a table, in which the assigned signal value y for the evaluation signal F is stored for each possible signal value x of the electromyogram signal E. However, the main parameter set may determine the parameters of a mathematical function, with which the corresponding signal value y of the evaluation signal is calculated from the signal value x of the electromyogram signal.

The signal values y of the evaluation signal F, which are contained in the table for the signal values x of the electromyogram signal E, are obtained in this preferred exemplary embodiment in a range around a base value in such a way that the signal values x are a function of the ratio of the probability $P_1(x)$ that the signal value x corresponds to the first state to the probability $P_2(x)$ that the signal value x corresponds to the second state.

In this preferred exemplary embodiment, this function is the logarithm, which is associated with the effect that when the probability $P_I(x)$ that the phase of inhalation is present is greater than the probability $P_E(x)$ that the phase of exhalation is present, the signal value y of the evaluation function is greater than zero. Conversely, the signal value y of the evaluation function is lower than zero when the probability $P_E(x)$ that the phase of exhalation is present is greater than the probability $P_I(x)$ that the phase of inhalation is present. This will later lead, in principle, to a simple possibility of determining which of the two phases or which of the two possible states is present by a threshold value analysis.

If the evaluation function is applied in the transformation step 9 to the electromyogram signal, the value corresponding to the table is assigned as the signal value y of the evaluation signal F to a signal value x of the electromyogram signal E, so that the evaluation signal F shown in FIG. 2 is obtained at first.

After the application of the evaluation function, the evaluation signal F thus generated is smoothed in the preferred exemplary embodiment being described here in a smoothing step 11 by treating each signal value y of the evaluation signal F as a predefined signal value y' and by each predefined signal value y' then being replaced by a mean value from signal values of the evaluation signal F, which may include the predefined signal value and include a first number of signal values y preceding the predefined signal value y' in time. Consequently, averaging is performed over a window that is running along (the signal course).

The term "mean value" shall also cover here, in the sense of the preset application, not only the arithmetic mean, but also values that are obtained with the use of a weighting function. In addition, also covered are values that are determined by the use of nonlinear smoothing methods such as rank order filters or median filters.

This means that the signal values y of the evaluation signal F are processed in such a way that they are treated as predefined signal values y' in the order in which the corresponding electromyogram signal values x were detected for them. A mean value is then formed for each predefined signal value y' from a first number of signal values y detected before the predefined signal value y' in time and the predefined signal value y' is replaced by this mean value. This means that the first number of signal values consists of values for which the above-described averaging was already performed. The evaluation signal G thus smoothed in the smoothing step 11 is likewise shown in FIG. 2.

The mean value is formed in the preferred embodiment of the method, which is being described here, in such a way that values located close to the predefined signal value y' in time are included in the averaging in a more heavily weighted form than those from the first number of signal values, which are located farther away in time from the predefined signal value y'. This leads to the advantage that despite the averaging, the smoothing step 11 does not lead to a great backward shifting in time of changes of the evaluation signal itself due to the smoothing step 11. It should also be noted that the term mean value in the sense of the present invention is not limited solely to the arithmetic mean, but it also covers other weighted means. In addition, the term "mean value" shall also cover values that are obtained by the application of nonlinear smoothing methods, such as rank order filters or median filters.

As is shown in FIG. 2, the height of the signal value y' of the smoothed evaluation signal G then indicates whether the electromyogram signal E corresponds to a first state or to a second state, i.e., whether the phase of inhalation or the phase of exhalation is present.

After carrying out the smoothing step 11, the generation proper of a control signal is performed within the control signal path 3 during step 5 to generate the control signal. This is carried out in the exemplary embodiment being described here by a threshold value comparison step 13, in which the signal values y' of the smoothed evaluation signal G are compared to the threshold value zero, as this is also shown in FIG. 2. The threshold value of zero is obtained in this exemplary embodiment from the selection of the logarithm as the function of the quotient of the probabilities $P_I(x)$ and $P_E(x)$ that a signal value of the electromyogram signal belongs to the phase of inhalation or to the phase of exhalation in the patient.

Thus, each signal value y' of the evaluation signal G, which is a smoothed signal in this case, is compared to a threshold value of zero during the generation of the control signal, and the control signal H shown in FIG. 2 assumes a first control value corresponding to the first state if the signal value y' of the smoothed evaluation signal G is above the threshold value, and the control signal H assumes a second control value corresponding to the second state if the signal value y' of the smoothed evaluation signal G is below the threshold value. The control signal H is then formed from signal values following one another in time and adapted to switch a ventilator into an inhalation operating mode if the evaluation signal corresponds to the first state and into an exhalation operating mode if the evaluation signal corresponds to the second state.

If the electromyogram signal E contains segments for which an analysis is not possible, for example, because an EKG signal is superimposed, the following possibilities are available in a preferred manner for handling this situation.

At first, the entire control signal path 3 may pause until analyzable or valid data are again detected at the input. It is also possible that the evaluation signal F is set to 0 in case of invalid or non-analyzable segments of the electromyogram signal E. The drawback of this is that after longer segments with invalid values, the first signal that is again valid alone sets the decision on whether the control signal H assumes one value or another. As a further alternative, the control signal path 3 may pause until valid data are again present at the input. The values of the evaluation signal F, which have become obsolete, are in the meantime removed from the smoothing filter step by step and to a certain degree.

Finally, artificial evaluation signal values, which are located in the vicinity of the neutral range of the evaluation signal F, i.e., at zero, may be generated in non-analyzable segments of the electromyogram signal E. In terms of value, these values are low, whose sign corresponds to the last detected hypothesis. The latter two possibilities are advantageous because the decision about a jump in the control signal H is not made absolutely by the first electromyogram signal value that is valid again, and, on the other hand, a jump is not delayed by many old evaluation signal values in the smoothing filter.

Simultaneously with the control signal path 3, at least one part of the electromyogram signal E previously freed from a constant background is processed in a secondary segmentation or analysis path 19 in order to determine the main parameter set used in the evaluation function in the control signal path 3. "Simultaneously" is defined in this connection such that the processing in the analysis path 19 takes place simultaneously with the generation of the control signal H in the control signal path 3.

An analysis segment E' (see FIG. 3), which is a part of the electromyogram signal E freed from the background, is analyzed in the analysis or secondary segmentation path 19 in a first analysis segment 21 in this exemplary embodiment at first with the evaluation function. The analysis segment E' is transformed for this into a second evaluation signal F' by applying the evaluation function to the analysis segment E', and a signal value Y of the second evaluation signal F' is assigned to a signal value of the analysis segment E' during the transformation. The evaluation function is determined in this case by an analysis parameter set, so that the analysis parameter set determines which signal value Y of the second evaluation signal F' is assigned to which signal value X of the analysis segment E' during the transformation with the application of the evaluation function.

The main parameter set, which is also used in the primary segmentation or control signal path 3 in step 5, is used as the analysis parameter set in the exemplary embodiment being described here. It is, however, also conceivable to apply another parameter set in the analysis path 19. In addition, the analysis parameter set and the renewed parameter set determined later are available as a table, so that the table of the main parameter set assigns a signal value Y of the second evaluation signal F' to each possible signal value X of the analysis segment E'.

After the transformation of the analysis segment E', the second evaluation signal F' thus generated is smoothed by each signal value Y of the second evaluation signal F' being treated, as was already explained in connection with step 11, as a predefined signal value Y' and by each predefined signal value Y' then being replaced by a mean value from signal values Y' of the second evaluation signal F', which signal values may include the predefined signal value Y' and which include a second number of signal values Y' located in time before the predefined signal value Y', but this second number is greater than the first number used in step 11. Due to the second number being greater than the first number, more intense smoothing is achieved, which increases the accuracy of the analysis in the analysis path 19. However, this is associated with a slower change in the smoothed second evaluation signal G' (see FIG. 3) during changes in the signal values of the analysis segment E' compared to the change in the evaluation signal F determined in the control signal path 3 in step 5.

As a result, the smoothed second evaluation signal G' is processed such that the height of a signal value Y' of this smoothed second evaluation signal G' indicates whether the corresponding signal value X of the analysis segment E' corresponds to a first state or to a second state, i.e., whether it belongs to the phase of inhalation or to the phase of exhalation.

Finally, an analysis signal I (see FIG. 3) is also generated in the first analysis segment 21 from the smoothed second evaluation signal G', which contains an analysis signal value A for each signal value X of the analysis segment E'. The analysis signal value A assumes a first value when the signal value Y' of the smoothed second evaluation signal G' that corresponds to the signal value X of the analysis segment E', for which the analysis signal value A shall be generated, is above a threshold value. In the preferred exemplary embodiment of a method according to the present invention, which embodiment is being described here, this threshold value is the value zero, because the evaluation function and the analysis or main parameter set is based on the function $\log(P_I(X)/P_E(X))$, $P_I(X)$ and $P_E(X)$ indicating the probabilities that a signal value X of the analysis segment E' corresponds to the first state, i.e., the phase of inhalation, or to the second state, i.e., the phase of exhalation.

The analysis signal value A then assumes a second value if the signal value Y' of the smoothed second evaluation signal G', which corresponds to the signal value X of the analysis segment E', for which the analysis signal value A is generated, is below this threshold value.

The signal representing the analysis segment E' is delayed in the delay step 23 taking place simultaneously with the first analysis step 21 such that it can be processed simultaneously with the analysis signal A generated in the first analysis step 21 in the second analysis step 25. This means that the delayed signal I of the analysis segment E' coincides with the entering analysis signal A such that a signal value X of the analysis segment E', for which the analysis signal value A was determined in the first analysis step 21, can be processed together with this analysis signal value A in the second analysis step 25. In particular, the analysis signal value A can then indicate directly for the signal value X of the analysis segment E' whether this signal value X belongs to the phase of inhalation or to the phase of exhalation.

A first frequency distribution $H_1(X)$ is then determined in the second analysis step 25 for the signal values X of the analysis segment, for which the analysis signal A assumes the first value and for which the smoothed second evaluation signal G' thus indicates that the first state is present. In addition, a second frequency distribution $H_2(X)$ is also determined simultaneously in the second analysis step 25 for the signal values X of the analysis segment E', for which signal values X the analysis signal A assumes the second value and the second evaluation signal G' therefor thus indicates that the second state is present.

Finally, a renewed parameter set is determined in the second analysis step 25 from the previously determined frequency distributions $H_1(X)$, $H_2(X)$. The renewed parameter set is designed as a table, which assigns a signal value of the evaluation signal to each possible signal value of the electromyogram signal E.

For a signal value of the electromyogram signal, which signal value is located in a range around a base value, the assigned signal value of the table is a function of the ratio of the value of the first frequency distribution $H_1((x)$ for the signal value x to the value of the second frequency distribution $H_2(x)$ for the signal value x in the exemplary embodiment being described here. The assigned signal value y is, in particular, proportional to the logarithm of the quotient of the frequency distributions, so that $y \propto \log(H_1((x)/H_2(x))$ is true for the values contained in the table for the signal value x. The base value is zero here due to the fact that a background changing slowly in this compared to the electromyogram signal is subtracted from the electromyogram signal in the exemplary embodiment being described here.

In addition, it should be noted that the frequency distribution $H_1(x)$ is a direct indicator of the probability $P_I(x)$, that the signal value x belongs to the phase of inhalation or corresponds to the first state, while the frequency distribution $H_2(x)$ is an indicator of the probability $P_E(x)$ that the signal value x belongs to the phase of exhalation or corresponds to the second state.

In the two marginal ranges, which are located outside the range around the base value, the table has a constant value ykonst, which is possibly different for each marginal range, for the corresponding signal values x of the electromyogram signal.

After conclusion of the generation of the renewed parameter set, whereby the second analysis step 25 is concluded, the renewed parameter set is transferred as a main parameter set to the control signal path 3 for use in step 5 in the transfer step marked by the arrow 27. Thus, the renewed parameter set is then used during the further determination of the control signal H for controlling the ventilator 7.

Since the analysis steps 21, 25 as well as the delay step 23 are carried out continuously simultaneously with the control signal path 3, the main parameter set used in the control signal path 3 is likewise adapted continuously in the method according to the present invention. This means that the determination of the parameter set takes place continuously in the secondary segmentation path, but the newly determined main parameter set is preferably transferred to the primary segmentation path at defined points in time only.

The evaluation function determined in the analysis path 19 or the parameter set permits indices that are important for the method to be determined.

An upwardly open function, which drops monotonically for negative values and rises monotonically for positive values, is expected as the basic form of the evaluation function or the evaluation signal values contained in the table. In addition, a negative result is expected for values that are low in terms of magnitude and a positive result is expected for values that are high in terms of magnitude.

Should the evaluation function not have any zeroes, this means that it is not possible to decide between the two states and this is indicative of erroneous signals. The possible case that there are more than two zeroes would be an indicator of artifacts and is not to be expected in case of signals having an approximately normal distribution.

In reference to the slope of the evaluation function as a function of the possible signal values, a monotonically rising slope is to be expected in case of normal signals. An especially great slope value (e.g., at the zeroes) is indicative of a very sharp separation of the two states, and an especially low slope value at the zeroes is indicative of a very blurred separation.

Only the value of the evaluation signal F is decisive in case of the artifact-free signals to be expected. A symmetry of the evaluation signal in relation to the Y axis is to be expected for this reason. By contrast, an asymmetry is again indicative of artifacts, for example, insufficiently removed QRS complex of the EKG signal.

The horizontal distance from the origin of the summit of the evaluation function is, as is to be expected for input values, equal to zero because signals that are free from mean value are assumed. The vertical shift must be negative, because there are otherwise no zeroes.

Finally, the deviation between the estimated evaluation function and a simplified mean square evaluation function can be determined, and a similarity to the square AMF is expected in case of an artifact-free signal. A deviation from the square shape means that the distributions deviate from the normal distribution.

Quality indices can be defined based on deviations of the described features of the evaluation function from the expected ones. The method can be checked for plausibility by means of the quality indices, and the method can be restarted in case of a negative result. Thus, a restart may take place, among other things, if the evaluation function is too flat or it mirrors against the abscissa compared to the expected form.

It also appears from the above that the exemplary embodiment of the device 2 according to the present invention for generating the control signal H has, in addition to the signal input 4, means provided in a control signal path 3 for transforming the electromyogram signal E into a smoothed evaluation signal G and means for generating the control signal H itself. The transforming means are also designed such that the main parameter set can be stored as a table in the device. In addition, means for transforming the analysis segment E' of the electromyogram signal E into the second evaluation signal F' by applying the evaluation function to the analysis step E' as well as means for determining the first and second frequency distributions $H_1(X)$, $H_2(X)$, means for determining the renewed parameter set and means for transferring the renewed parameter set are provided in the device, and the means for transforming the analysis segment E', the means for determining the first and second frequency distributions $H_1(X)$, $H_2(X)$, the means for determining the renewed parameter set and the means for transferring the renewed parameter set are designed to operate simultaneously with the means for transforming the electromyogram signal E and with the means for generating the control signal H. In addition, means with which the above-described analysis signal A is generated are provided in the device.

Figure 3:
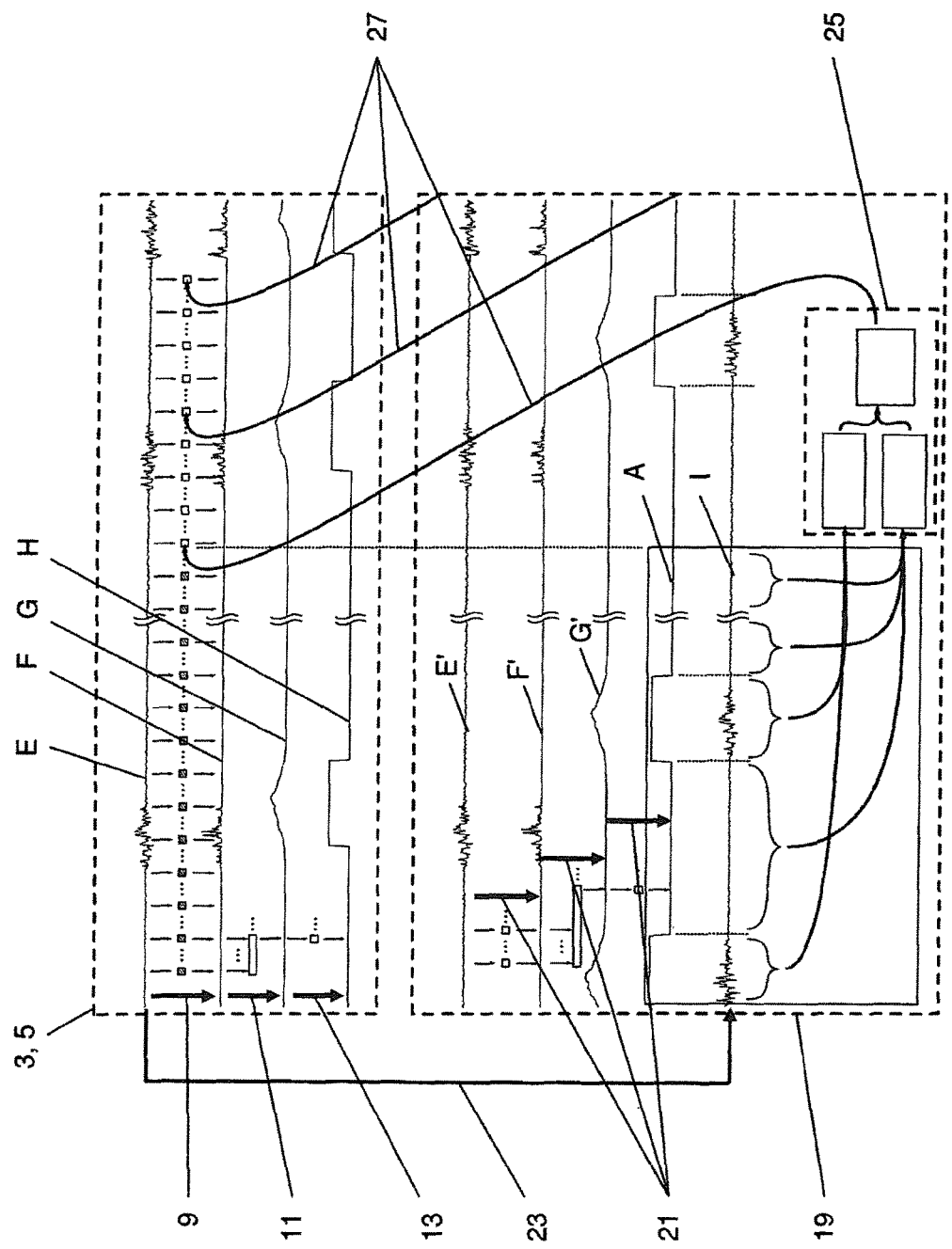
FIG. 3 is a schematic view of the course of the method together with the corresponding signals as a function of time.

The preferred exemplary embodiment of the method according to the present invention and the device 2 according to the present invention have been described so far essentially on the basis of FIGS. 1 and 2. FIG. 3 shows the process once again on the basis of the signals generated thereby, the signals being shown chronologically simultaneously one above the other, so that it can be seen that the process is accelerated in the control signal path 3 compared to the analysis path 19.

Specifically, it can also be seen once again in FIG. 3 that the signals F, G and G generated in the steps 9, 11 and 13 from the electromyogram signal E are arranged chronologically simultaneously in the primary segmentation or control signal path 3, which is represented here by a box. It is seen that the maximum in the smoothed evaluation signal G is slightly shifted in time by the amount ΔT compared to the corresponding deflections in the evaluation signal F because of the smoothing step 11. The result of this is then that the transition of the control signal H from the first control value 15 to the second control value 17 is likewise delayed slightly in time compared to the deflections in the evaluation signal G or the electromyogram signal E. However, this delay is not of a great disadvantage, because the deflections in the electromyogram signal appear so early compared to other breathing-relevant physiological signals that the switchover of the ventilator always takes place in time for the patient. In addition, the quality of the determination of the transition from the phase of exhalation to the phase of inhalation is significantly improved by the smoothing.

Furthermore, it can be seen in FIG. 3 that the process taking place in the analysis path 19 is delayed compared to the control signal path 3, because averaging is performed over a larger second number of signal values Y' of the second evaluation signal F' in the first analysis step 21 during the smoothing of the second evaluation signal F' and the generation of the smoothed second evaluation signal G'. However, the higher quality thus achieved in the determination of the frequency distributions $H_1(x)$, $H_2(x)$ in step 21 does not lead to a slowdown in generating the control signal H, because this takes place in the control signal path 3.

In addition, it can be seen that the analysis segment E' in the delay step 23 is delayed in time such that the delayed signal I of the analysis segment E' is sent to the second analysis segment 25 simultaneously in such a way that a signal value X of the analysis segment E' is processed simultaneously with the signal value of the analysis signal A, which latter signal value was generated for this signal value X in the first analysis step 21. The analysis signal A thus represents an indicator indicating that the signal values X of the analysis segment E' belong to the first or second state or to the phase of inhalation or to the phase of exhalation.

Figure 4:
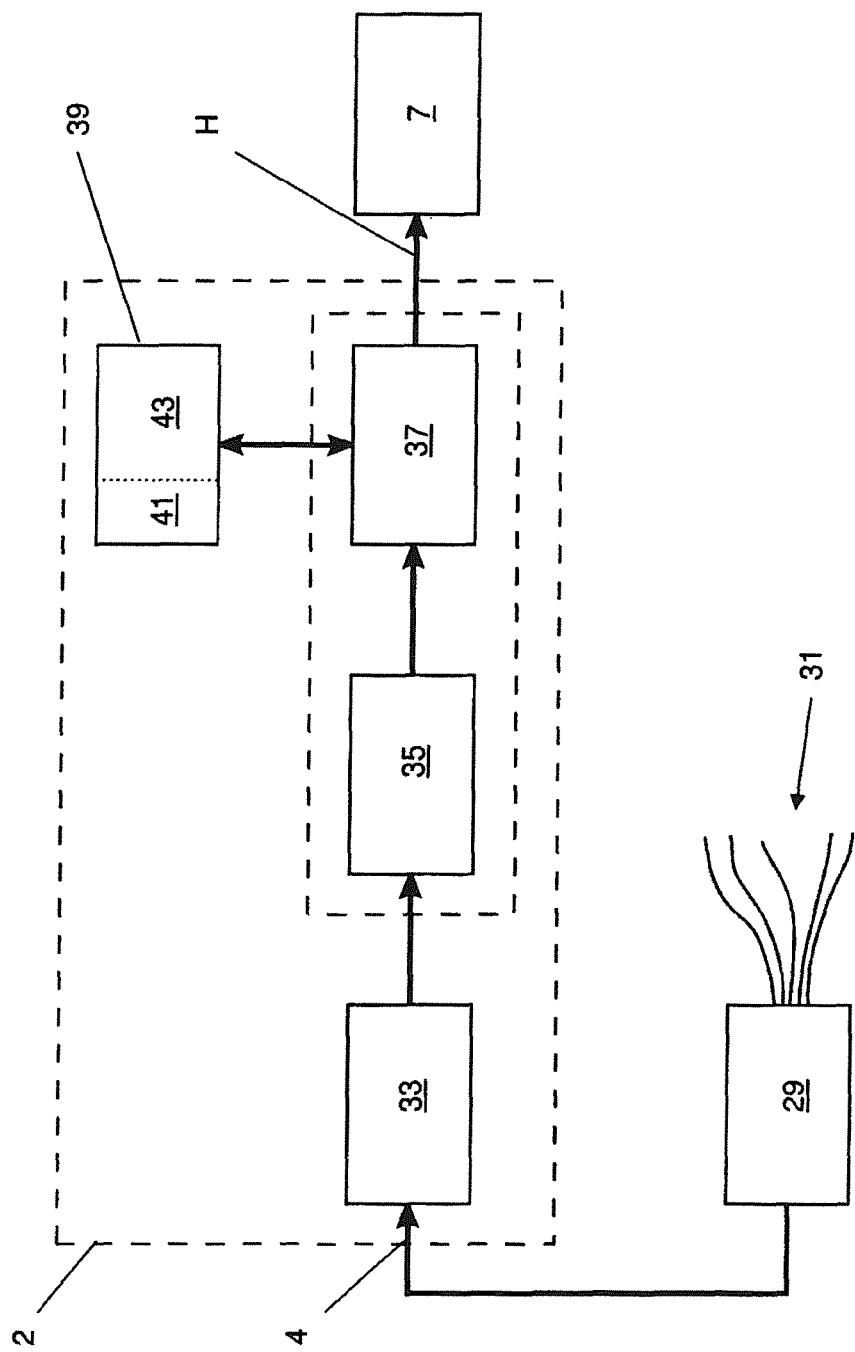
FIG. 4 is a schematic view of an exemplary embodiment of a device according to the present invention for generating a control signal.

FIG. 4 schematically shows the design of an exemplary embodiment of the device 2 according to the present invention for generating a control signal H for a ventilator 7 according to the above-described method. The device has a signal input 4, with which electromyogram signals E amplified by a preamplifier 29, which were picked up by means of electrodes 31, are detected. The device 2 comprises, first, an analog-digital converter 33 for digitizing the electromyogram signal E. The converter 33 is followed downstream by a signal processor 35, with which the entering electromyogram signal E is subjected to preprocessing by, for example, subtracting a low-frequency background and removing signal components that are obvious artifacts.

The processor 37 proper, which accesses a memory 39, in which the program for processing the entering data is stored in a program memory 41 and in which the parameter sets are stored in a data memory 43, is, in turn, arranged downstream of the signal processor 35. Together with the memory 39, the means for transforming the electromyogram signal E into an evaluation signal F by applying an evaluation function to the electromyogram signal E are thus provided by the processor 37, and a signal value y of the evaluation signal F, which signal value is stored in the data memory 43, is assigned to a signal value x of the electromyogram signal E during the transformation. This signal value y is determined by the main parameter set stored as a table in the data memory 43. In addition, the processor 37 also represents the means with which the control signal H, with which the ventilator 7 is switched into an inhalation operating mode or an exhalation operating mode, is generated.

Finally, the means for the above-described transformation of an analysis segment E' of the electromyogram signal E into a second evaluation signal F' by applying the evaluation function to the analysis segment E' are also embodied by the processor 37 together with the data memory 43, the evaluation function F' being determined by an analysis parameter set stored in the data memory 43. The first frequency distribution $H_1(X)$ and the second frequency distribution $H_2(X)$ for the signal values X of the evaluation signal F' are determined by the processor 37 and the data memory 43 in the above-described manner, and a renewed parameter set, which is transferred as a main parameter set, is determined from this. This is carried out by the processor 37 simultaneously with the transformation of the electromyogram signal E and the generation of the control signal H.

On the whole, the above-described method as well as the device 2 designed according to the present invention make it possible in a reliable manner to generate a control signal H for the ventilator 7 from an electromyogram signal E, and this takes place at a sufficiently high processing speed, without this being to the detriment of accuracy.

In addition, the method and the parameters being stored in the data memory adjust adaptively to changes in the conditions, because the parameter set necessary for assigning the electromyogram signal segments to the phase of inhalation or to the phase of exhalation is determined continuously anew.

While specific embodiments of the invention have been shown and described in detail to illustrate the application of the principles of the invention, it will be understood that the invention may be embodied otherwise without departing from such principles.

The invention claimed is:

1. A method for generating a control signal for a ventilator, the method comprising the steps of:

providing a main parameter set;

detecting an electromyogram signal, which comprises signal values following one another in time;

transforming the electromyogram signal into an evaluation signal by applying an evaluation function to the electromyogram signal, wherein during the transformation a signal value of the evaluation signal is assigned to a signal value of the electromyogram signal during the transformation, wherein the evaluation function is determined by the main parameter set, so that the main parameter set establishes which signal value of the evaluation signal is assigned to which signal value of the electromyogram signal during the transformation when applying the evaluation function, and wherein a position of the signal value of the evaluation signal relative to a base value indicates whether the electromyogram signal corresponds with an inhalation phase or corresponds with an exhalation phase and wherein the signal value of the evaluation signal is assigned, when applying the evaluation function, from a range of signal values of the electromyogram signal around the base value, and the evaluation function is the logarithm of a ratio of a probability that the signal value of the electromyogram signal belongs to the inhalation phase to a probability that the signal value of the electromyogram signal belongs to the exhalation phase; and generating a control signal from signal values of the evaluation signal following one another in time, which is adapted to switch the ventilator into an inhalation operating mode if the evaluation signal corresponds to the inhalation phase and into an exhalation operating mode if the evaluation signal corresponds to the exhalation phase;

analyzing at least a portion of the electromyogram signal for adapting the main parameter set to a renewed parameter set for subsequent transformation, the analyzing comprising:

providing an analysis parameter set;

transforming an analysis segment of the electromyogram signal into a second evaluation signal by applying an analysis evaluation function to the analysis segment, wherein during the analysis segment transformation, a signal value of the second evaluation signal is assigned to a signal value of the analysis segment, wherein the analysis evaluation function is determined by the analysis parameter set so that the analysis parameter set establishes which signal value of the second evaluation signal is assigned to which signal value of the analysis segment during the analysis segment transformation when applying the analysis evaluation function, and wherein a height of the signal value of the second evaluation signal indicates whether the corresponding signal value of the analysis segment corresponds to an inhalation phase or an exhalation phase;

determining a first frequency distribution of signal values from the analysis segment for which the second evaluation signal indicates that the inhalation phase is present;

determining a second frequency distribution of signal values from the analysis segment for which the second evaluation signal indicates that the exhalation phase is present;

determining the renewed parameter set from the determined first frequency distribution and the determined second frequency distribution; and replacing the main parameter set with the renewed parameter set, to provide the renewed parameter set as the main parameter set, wherein determining the first frequency distribution and the second frequency distribution, determining the renewed parameter set and transferring the renewed parameter set, proceed in parallel with the transforming of the electromyogram signal and the generating of the control signal.

2. A method in accordance with claim 1, wherein:
the electromyogram signal or the evaluation signal is smoothed during the transformation by each signal value of the electromyogram signal or of the evaluation signal being treated as a predefined signal value; and
each predefined signal value of the electromyogram signal or of the evaluation signal is replaced by a mean value from signal values of the electromyogram signal or of the evaluation signal, which may include the predefined signal value and include a first number of signal values located in time before the predefined signal value.

3. A method in accordance with claim 1, wherein:
the main parameter set is provided as a table, in which the assigned signal value for the evaluation signal is contained for each possible signal value of the electromyogram signal; and
the value corresponding to the table is assigned as a signal value of the evaluation signal based on a signal value of the electromyogram signal during the application of the evaluation function.

4. A method in accordance with claim 1, wherein:
each signal value of the evaluation signal is compared with a threshold value during the generation of the control signal;
the control signal assumes a first control value if the signal value of the evaluation signal is above the threshold value, which first control value corresponds to the inhalation operating mode; and
the control signal assumes a second control value if the signal value of the evaluation signal is below the threshold value, which second control value corresponds to the exhalation operating mode.

5. A method in accordance with claim 1, wherein the main parameter set is used as the analysis parameter set.

6. A method in accordance with claim 1, wherein:
the electromyogram signal or the evaluation signal is smoothed during the transformation by each signal value of the electromyogram signal or of the evaluation signal being treated as a predefined signal value and by each predefined signal value of the electromyogram signal or of the evaluation signal being replaced by a mean value from signal values of the electromyogram signal or of the evaluation signal, which may include the predefined signal value and include a first number of signal values located in time before the predefined signal value;

the second evaluation signal is smoothed after the transformation of the analysis segment by each signal value of the second evaluation signal being treated as a predefined signal value and by each predefined signal value of the second evaluation signal being replaced by a mean value from signal values of the second evaluation signal, which may include the predefined signal value and which include a second number of signal values located preceding in time the predefined signal value; and the second number is greater than the first number.

7. A method in accordance with claim 6, wherein:
an analysis signal is generated, which contains an analysis signal value for each signal value of the analysis segment;
an analysis signal value assumes a first value if the signal value of the second evaluation signal that corresponds to the signal value of the analysis segment for which the analysis signal value is generated, is above a threshold value;
an analysis signal value assumes a second value if the signal value of the second evaluation signal, which corresponds to the signal value of the analysis segment for which the analysis signal value is generated, is below a threshold value;
the first frequency distribution is determined for the signal values of the analysis segment for which the analysis signal value has the first value; and
the second frequency distribution is determined for the signal values of the analysis segment for which the analysis signal value has the second value.

8. A method in accordance with claim 1, wherein:
the main parameter set is available as a table, in which the assigned signal value for the evaluation signal is contained for each possible signal value of the electromyogram signal;
the value corresponding to the table is assigned as a signal value of the evaluation signal to a signal value of the electromyogram signal during the application of the evaluation function;
the renewed parameter set is designed as a table, which assigns a signal value of the evaluation signal to each possible signal value of the electromyogram signal; and
the assigned signal value of the table for a signal value of the electromyogram signal, which signal value is located in a range around a base value, is a function of the ratio of the value of the first frequency distribution for the signal value to the value of the second frequency distribution for the signal value.

9. A method in accordance with claim 8, wherein the assigned signal value has a constant value for signal values of the electromyogram signal from a marginal range, which is outside the range.

10. A device for generating a control signal for a ventilator, which device has a signal input for input of an electromyogram signal, which electromyogram signal includes signal values following one another in time, the device comprising:
means for providing a main parameter set;
means for transforming the electromyogram signal into an evaluation signal by applying an evaluation function to the electromyogram signal, wherein a signal value of the evaluation signal is assigned to a signal value of the electromyogram signal during the transformation, wherein the evaluation function is determined by the main parameter set, so that the main parameter set establishes which signal value of the evaluation signal is assigned to which signal value of the electromyogram signal during the transformation when applying the evaluation function, and wherein a position of the signal value of the evaluation signal relative to a base value indicates whether the electromyogram signal corresponds with an inhalation phase or corresponds with an exhalation phase and wherein a signal value of the evaluation signal is assigned, when applying the evaluation function, from a range of signal values of the electromyogram signal around the base value, and the evaluation function is the logarithm of a ratio of a probability that the signal value of the electromyogram signal belongs to the inhalation phase to a probability that the signal value of the electromyogram signal belongs to the exhalation phase;

means for generating a control signal from signal values of the evaluation signal following one another in time, which control signal is adapted to switch the ventilator into an inhalation operating mode if the evaluation signal corresponds to the inhalation phase and to switch the ventilator into an exhalation operating mode if the evaluation signal corresponds to the exhalation phase;

means to analyze at least a portion of the electromyogram signal for adapting the main parameter set to a renewed parameter set for subsequent transformation, the means to analyze comprising:

means for providing an analysis parameter set;

means for transforming an analysis segment of the electromyogram signal into a second evaluation signal by applying an analysis evaluation function to the analysis segment, wherein during the analysis segment transformation, a signal value of the second evaluation signal is assigned to a signal value of the analysis segment, wherein the analysis evaluation function is determined by the analysis parameter set so that the analysis parameter set establishes which signal value of the second evaluation signal is assigned to which signal value of the analysis segment during the analysis segment transformation when applying the analysis evaluation function, and wherein a height of the signal value of the second evaluation signal indicates whether the corresponding signal value of the analysis segment corresponds to an inhalation phase or an exhalation phase;

means for determining a first frequency distribution of signal values from the analysis segment for which the second evaluation signal indicates that the inhalation phase is present;

means for determining a second frequency distribution of signal values from the analysis segment for which the second evaluation signal indicates that the exhalation phase is present;

means for determining the renewed parameter set from the determined first frequency distribution and the determined second frequency distribution; and means for replacing the main parameter set with the renewed parameter set, to provide the renewed parameter set as the main parameter set, wherein the means for determining the first frequency distribution and the second frequency distribution, the means for determining the renewed parameter set and the means for transferring the renewed parameter set are configured to operate in parallel to the means for transforming the electromyogram signal and the means for generating the control signal.

11. A device in accordance with claim 10, wherein:

the transformation means is configured such that the main parameter set is stored as a table, in which the assigned signal value for the evaluation signal is contained for each possible signal value of the electromyogram signal; and the value corresponding to the table is assigned as a signal value of the evaluation signal to a signal value of the electromyogram signal when the evaluation function is applied.

12. A device in accordance with claim 10, further comprising means for generating an analysis signal, which contains an analysis signal value for each signal value of the analysis segment, wherein:

an analysis signal value assumes a first value if the signal value of the second evaluation signal, which corresponds to the signal value of the analysis segment, for which the analysis signal value is generated, is above a threshold value;

an analysis signal value assumes a second value if the signal value of the second evaluation signal, which corresponds to the signal value of the analysis segment, for which the analysis signal value is generated, is below a threshold value; and the means for determining the frequency distributions are adapted such that the first frequency distribution is determined for the signal values of the analysis segment for which the analysis signal value has the first value, and the second frequency distribution is determined for the signal values of the analysis segment for which the analysis signal value has the second value.

13. A device in accordance with claim 10, wherein:

each signal value of the evaluation signal is compared with a threshold value during the generation of the control signal;

the control signal assumes a first control value if the signal value of the evaluation signal is above the threshold value, which first control value corresponds to the inhalation operating mode; and the control signal assumes a second control value if the signal value of the evaluation signal is below the threshold value, which second control value corresponds to the exhalation operating mode.

\* \* \* \* \*